US010383583B2

(12) United States Patent
Tomomura et al.

(10) Patent No.: US 10,383,583 B2
(45) Date of Patent: Aug. 20, 2019

(54) X-RAY CT APPARATUS

(71) Applicant: Toshiba Medical Systems Corporation, Otawara-shi (JP)

(72) Inventors: Kenji Tomomura, Nasushiobara (JP); Katsumi Gotanda, Nasushiobara (JP); Takeo Nabatame, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 361 days.

(21) Appl. No.: 15/293,994

(22) Filed: Oct. 14, 2016

(65) Prior Publication Data
US 2017/0105690 A1 Apr. 20, 2017

(30) Foreign Application Priority Data

Oct. 16, 2015 (JP) .................................. 2015-204940
Oct. 13, 2016 (JP) .................................. 2016-202091

(51) Int. Cl.
*A61B 6/00* (2006.01)
*A61B 6/03* (2006.01)
*A61B 6/08* (2006.01)

(52) U.S. Cl.
CPC .............. *A61B 6/032* (2013.01); *A61B 6/08* (2013.01); *A61B 6/467* (2013.01); *A61B 6/545* (2013.01)

(58) Field of Classification Search
None
See application file for complete search history.

(56) References Cited

U.S. PATENT DOCUMENTS

2013/0156151 A1* 6/2013 Sugaya ................. A61B 6/032
378/16
2015/0164440 A1* 6/2015 Rackow .............. A61B 5/7485
600/427

FOREIGN PATENT DOCUMENTS

| JP | 2002-272723 | 9/2002 |
| JP | 2003-047608 | 2/2003 |
| JP | 2007-97776 | 4/2007 |

* cited by examiner

*Primary Examiner* — Hoon K Song
(74) *Attorney, Agent, or Firm* — Oblon, McClelland, Maier & Neustadt, L.L.P.

(57) ABSTRACT

An X-ray CT apparatus includes a processing circuit. The processing circuit adjusts an image taking area of a subject by receiving an operation performed on a light projector provided on a gantry and further sets the adjusted image taking area as an image taking condition included in first image taking conditions; adjusts an image taking area of the subject by receiving an operator's operation via terminal equipment and further sets the adjusted image taking area as an image taking condition included in second image taking conditions; and causes the gantry to perform the image taking process on the basis of selection information selecting from between the first and the second image taking conditions as image taking conditions used for performing the image taking process.

12 Claims, 7 Drawing Sheets

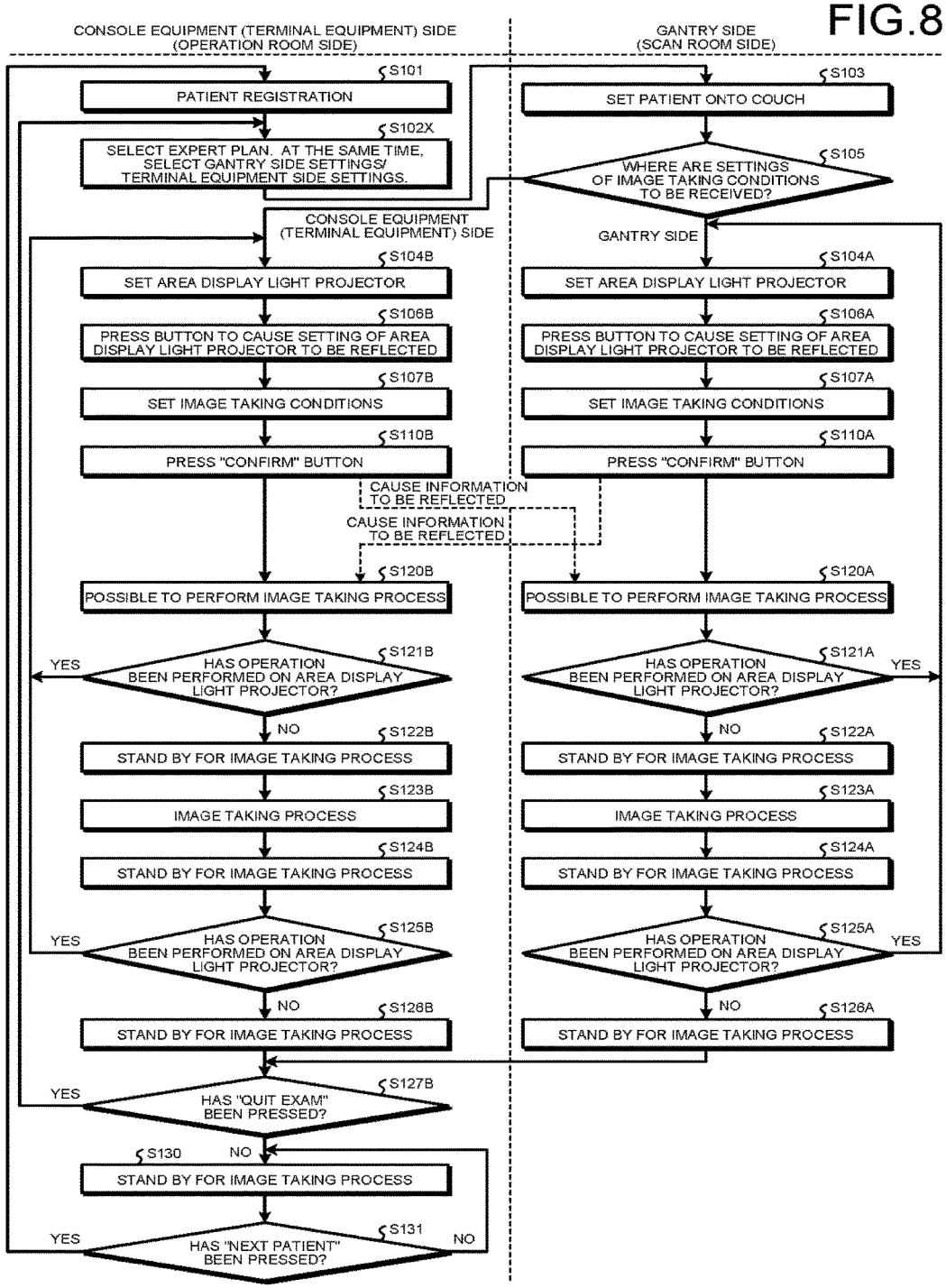

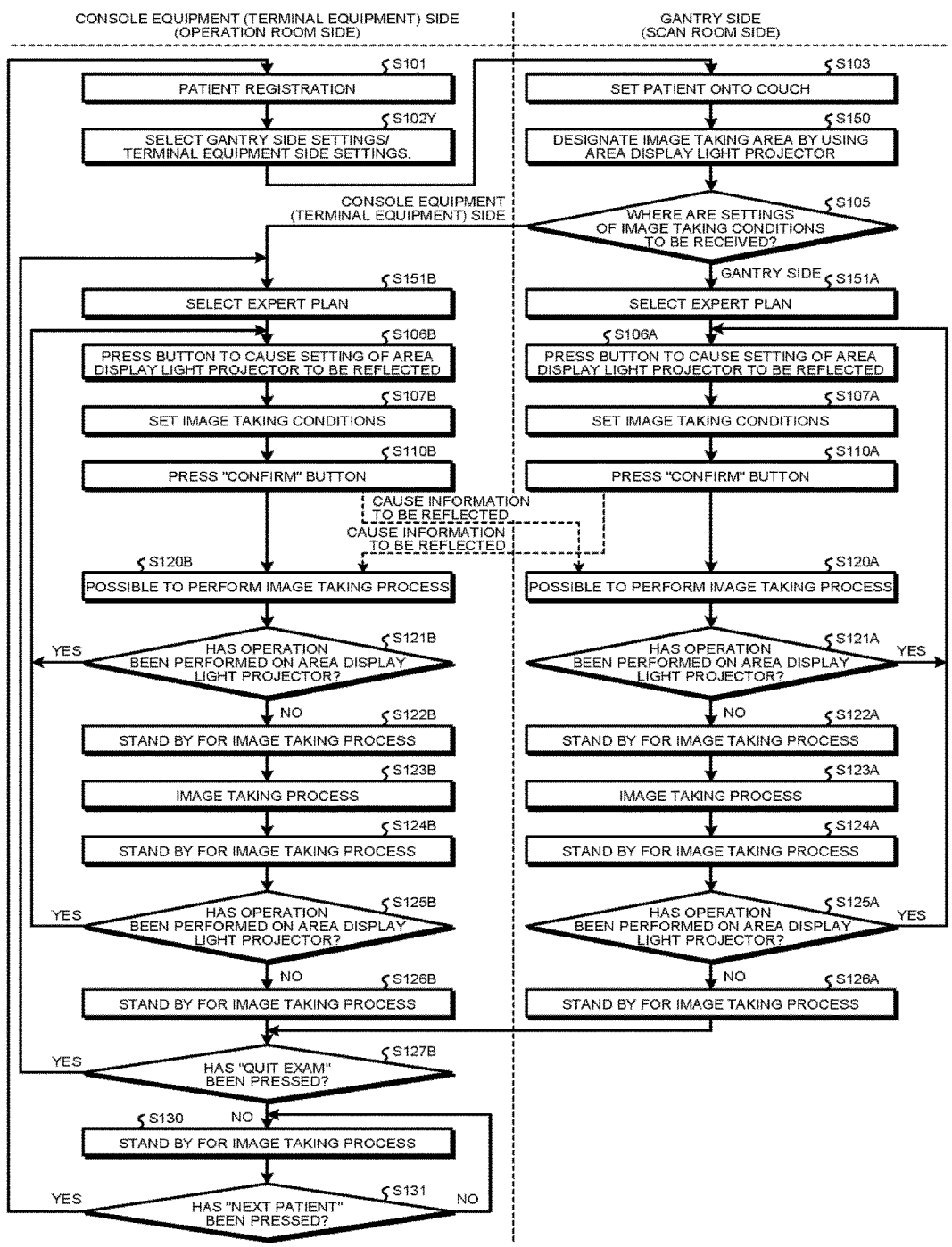

X-RAY CT APPARATUS

CROSS-REFERENCE TO RELATED APPLICATIONS

This application is based upon and claims the benefit of priority from Japanese Patent Application No. 2015-204940, filed on Oct. 16, 2015 and Japanese Patent Application No. 2016-202091, filed on Oct. 13, 2016, the entire contents of all of which are incorporated herein by reference.

FIELD

Embodiments described herein relate generally to an X-ray CT apparatus.

BACKGROUND

Examples of methods used for performing image taking processes by using an X-ray Computed Tomography (CT) apparatus include a method by which image taking conditions are set on the side of terminal equipment (a console equipment) and another method by which image taking conditions are set on the side of a scan room (a gantry).

However, when an X-ray CT apparatus is configured to make it possible to set the image taking conditions both on the side of the gantry (hereinafter, "gantry side") and on the side of the console equipment (hereinafter, "console equipment side"), there is a possibility that an image taking process may be performed by using image taking conditions that are not intended by the operator, unless it is clearly defined which side (either the gantry side or the console equipment side) provides information used for setting the image taking conditions.

BRIEF DESCRIPTION OF THE DRAWINGS

FIG. 8 is a flowchart for explaining a flow in a process performed by an X-ray CT apparatus according to a second embodiment; and FIG. 9 is a flowchart for explaining a flow in a process performed by an X-ray CT apparatus according to a third embodiment.

DETAILED DESCRIPTION

An X-ray CT apparatus according to an embodiment includes a processing circuit. The processing circuit adjusts an image taking area of a subject by receiving an operation performed on a light projector provided on a gantry and to set the adjusted image taking area as an image taking condition included in first image taking conditions, the gantry being configured to perform a CT image taking process on the subject with X-rays; adjusts an image taking area of the subject by receiving an operation from an operator via terminal equipment and to set the adjusted image taking area as an image taking condition included in second image taking conditions; and causes the gantry to perform the image taking process on the basis of selection information selecting from between the first image taking conditions and the second image taking conditions as image taking conditions used for performing the image taking process on the subject.

Exemplary embodiments of the X-ray CT apparatus will be explained in detail below, with reference to the accompanying drawings. There are various types of X-ray CT apparatuses including: a Rotate/Rotate type in which an X-ray tube and an X-ray detector together rotate around a subject; and a Stationary/Rotate type in which a large number of X-ray detecting elements arrayed in a ring formation are fixed, while only an X-ray tube rotates around a subject. The embodiments described herein are applicable to any type. Further, in recent years, what is called multi-tube X-ray CT apparatuses in which a plurality of pairs each made up of an X-ray tube and an X-ray detector are installed on a rotating frame have been commercialized as products, and technology related to those products is being developed. The embodiments described herein are applicable to both conventional single-tube X-ray CT apparatuses and multi-tube X-ray CT apparatuses. In the embodiments described below, a single-tube Rotate/Rotate-type X-ray CT apparatus will be explained as an example.

First Embodiment

Figure 1:
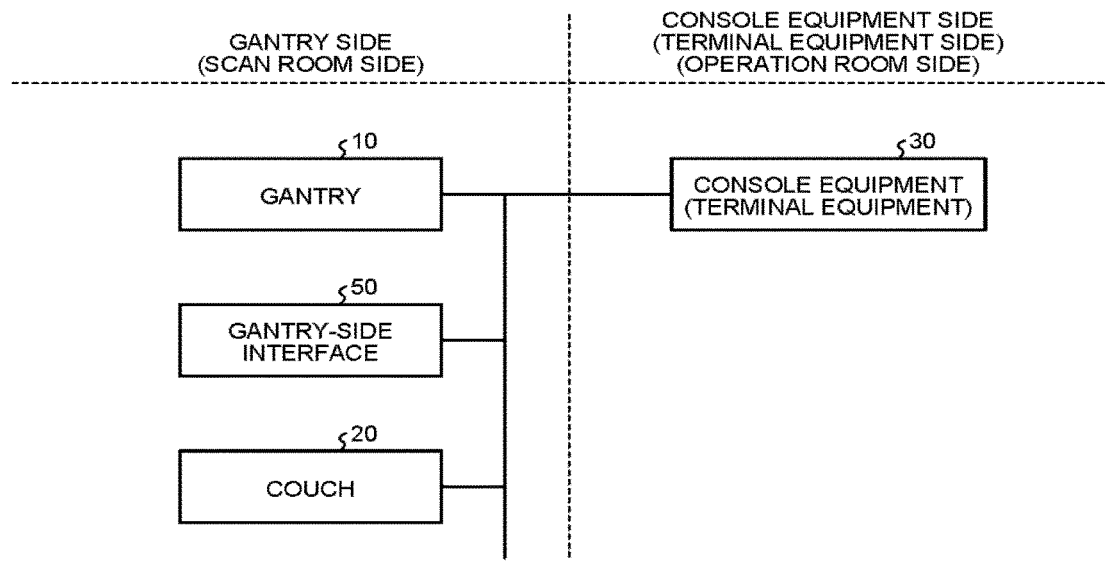
FIGS. 1 to 5 are block diagrams illustrating an exemplary configuration of an X-ray CT apparatus according to an embodiment.

First, outlines of constituent elements of an X-ray CT apparatus according to a first embodiment will be explained, with reference to FIGS. 1 to 5. FIGS. 1 to 5 are block diagrams illustrating an exemplary configuration of the X-ray CT apparatus according to the embodiment. As illustrated in FIG. 1, the X-ray CT apparatus according to the embodiment includes a gantry 10, a couch 20, a gantry-side interface 50, and console equipment 30. The gantry 10, the gantry-side interface 50, and the couch 20 are provided on the scan room side, whereas the console equipment 30 (terminal equipment) is provided on the operation room side. The gantry-side interface 50 may be installed near the gantry 10 or may integrally be formed with the gantry 10 while being assembled in the gantry 10.

Figure 2:
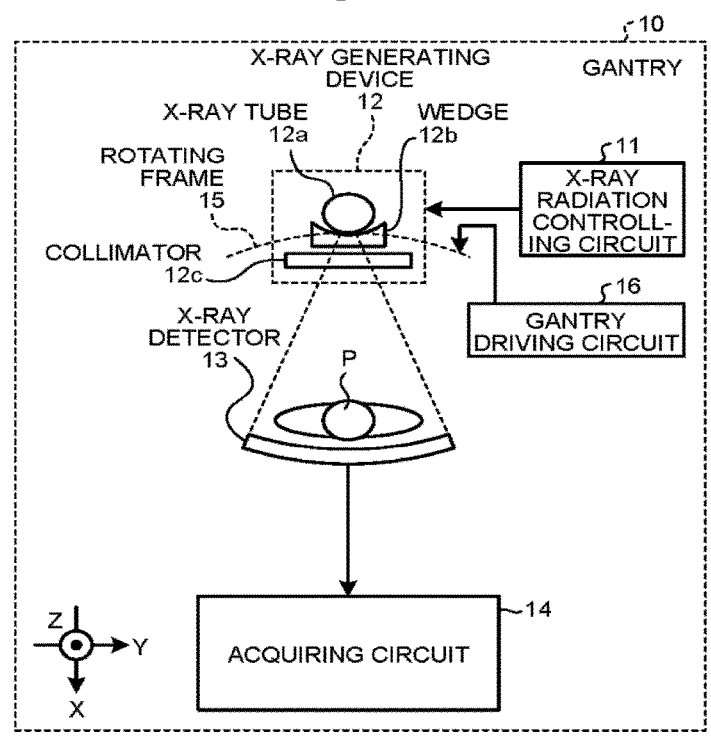

FIG. 2 illustrates a schematic configuration of the gantry 10. The gantry 10 is a device configured to radiate X-rays to a subject P and to acquire projection data from detection data of X-rays that have passed through the subject P. The gantry 10 includes an X-ray radiation controlling circuit 11, X-ray generating equipment (an X-ray generating device) 12, an X-ray detector 13, an acquiring circuit 14, a rotating frame 15, and a gantry driving circuit 16.

The rotating frame 15 is configured to support the X-ray generating equipment 12 including an X-ray tube 12a (explained later) and the X-ray detector 13 so as to be rotatable around the subject P. The rotating frame 15 is an annular frame configured to support the X-ray generating equipment 12 and the X-ray detector 13 so as to oppose each other while the subject P is interposed therebetween and configured to be rotated by the gantry driving circuit 16 (explained later) at a high speed on a circular orbit centered on the subject P.

The X-ray generating equipment 12 is a device configured to generate the X-rays and to radiate the generated X-rays onto the subject P and includes the X-ray tube 12a, a wedge 12b, and a collimator 12c.

The X-ray tube 12a is configured to radiate the X-rays. More specifically, the X-ray tube 12a is a vacuum tube configured to generate X-ray beams onto the subject P by using a high voltage supplied by the X-ray radiation controlling circuit 11 (explained later). The X-ray tube 12a radiates the X-ray beams onto the subject P, as the rotating frame 15 rotates. The X-ray tube 12a generates the X-ray beams that spread with a fan angle or a cone angle.

The wedge 12b is an X-ray filter configured to adjust the X-ray dose of the X-rays radiated from the X-ray tube 12a. Under control of the X-ray radiation controlling circuit 11 (explained later), the collimator 12c is a slit configured to narrow down the radiation range of the X-rays of which the X-ray dose has been adjusted by the wedge 12b.

The X-ray radiation controlling circuit 11 is a device serving as a high-voltage generating unit and configured to supply the high voltage to the X-ray tube 12a. The X-ray tube 12a is configured to generate the X-rays by using the high voltage supplied from the K-ray radiation controlling circuit 11. The X-ray radiation controlling circuit 11 is configured to adjust the X-ray dose radiated onto the subject P, by adjusting the X-ray tube voltage and the X-ray tube current supplied to the X-ray tube 12a. Further, the X-ray radiation controlling circuit 11 is configured to adjust the radiation range (the fan angle or the cone angle) of the X-rays, by adjusting the opening degree of the collimator 12c.

The gantry driving circuit 16 is configured to cause the X-ray generating equipment 12 and the X-ray detector 13 to revolve on the circular orbit centered on the subject P, by driving the rotating frame 15 to rotate.

The X-ray detector 13 is configured to detect the X-rays that were radiated from the X-ray tube 12a and have passed through the subject P. More specifically, the X-ray detector 13 is configured to detect the X-rays that were radiated from the X-ray tube 12a and have passed through the subject P, by employing X-ray detecting elements arranged two-dimensionally. The X-ray detector 13 illustrated in FIG. 2 is a two-dimensional-array-type detector (a planar detector) configured to output X-ray intensity distribution data indicating an intensity distribution of the X-rays that have passed through the subject P. In the X-ray detector 13, a plurality of rows of X-ray detecting elements are arranged along the body axis direction of the subject P (i.e., along the Z-axis direction in FIG. 2), while each row (each detecting element row) contains a plurality of X-ray detecting elements arranged along the channel direction (i.e., along the Y-axis direction in FIG. 2). For example, the X-ray detector 13 includes 320 rows of detecting elements arranged along the body axis direction of the subject P, so as to detect, in a wide range, the X-ray intensity distribution data of the X-rays that have passed through the subject P.

The acquiring circuit 14 is realized with a Data Acquisition System (DAS) and is configured to acquire the projection data from the X-ray detection data detected by the X-ray detector 13. For example, the acquiring circuit 14 generates the projection data by performing an amplifying process, an Analog/Digital (A/D) converting process, a sensitivity correcting process among the channels, and the like on the X-ray intensity distribution data detected by the X-ray detector 13 and further transmits the generated projection data to the console equipment 30 (explained later).

For example, when the X-rays are continuously radiated from the X-ray tube 12a while the rotating frame 15 is rotating, the acquiring circuit 14 acquires pieces of projection data corresponding to the entire circumference (corresponding to 360 degrees). Further, the acquiring circuit 14 brings the acquired pieces of projection data into correspondence with X-ray tube positions and further transmits the result to the console equipment 30 (explained later). The X-ray tube positions serve as information indicating the projection directions of the pieces of projection data. As additional information, the sensitivity correcting process among the channels may be performed by a processing circuit 40B (explained later) by employing a pre-processing function 34.

Figure 3:
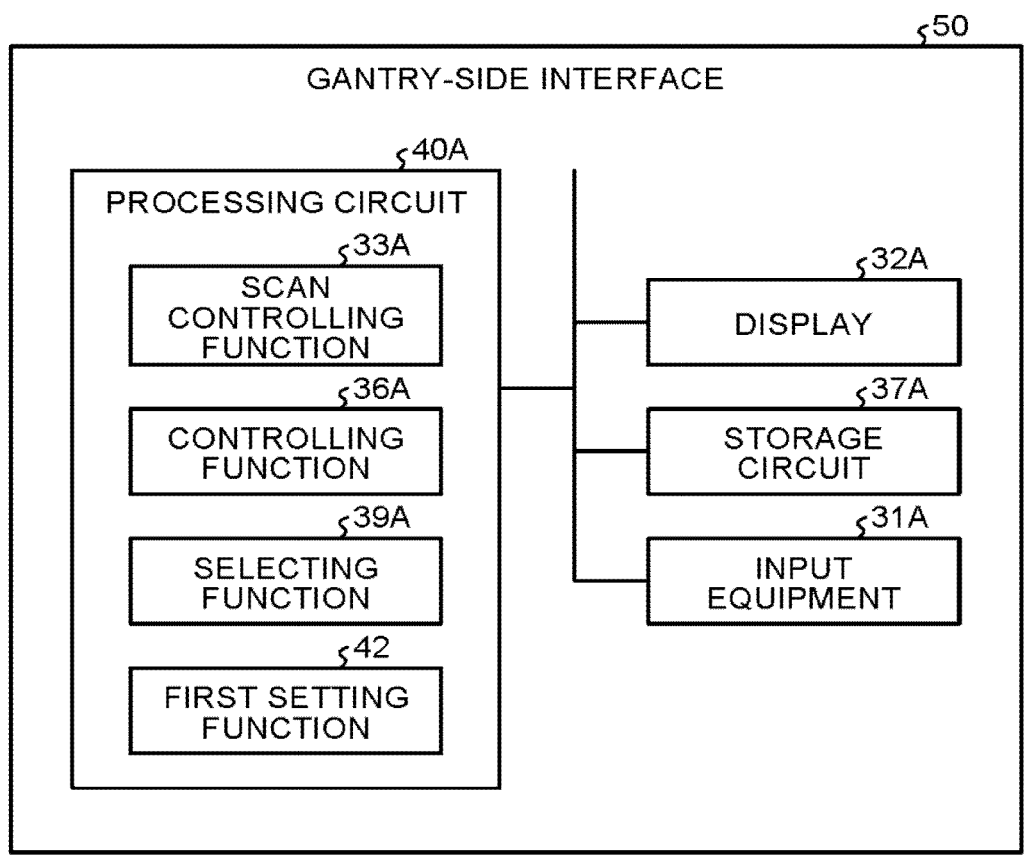

FIG. 3 illustrates a schematic configuration of the gantry-side interface 50. The gantry-side interface 50 is a device configured to receive, on the scan room side, operations performed on the X-ray CT apparatus from the operator. The gantry-side interface 50 includes, for example, a display 32A, a storage circuit 37A, input equipment 31A, and a processing circuit 40A. The processing circuit 40A includes, for example, a scan controlling function 33A, a controlling function 36A, a selecting function 39A, and a first setting function 42.

In an embodiment, processing functions implemented by constituent elements such as the scan controlling function 33A, the controlling function 36A, the selecting function 39A, and the first setting function 42 are stored in the storage circuit 37A in the form of computer-executable programs. The processing circuit 40A is a processor configured to realize the functions corresponding to the programs by reading and executing the programs from the storage circuit 37A. In other words, it means that the processing circuit 40A that has read the programs has the functions illustrated within the processing circuit 40A in FIG. 3.

FIG. 3 illustrates the example in which the single processing circuit 40A realizes the processing functions implemented by the scan controlling function 33A, the controlling function 36A, the selecting function 39A, and the first setting function 42; however, another arrangement is acceptable in which the processing circuit 40A is structured by combining together a plurality of independent processors, so that the processors realize the functions by executing the programs. In other words, each of the functions described above may be configured as a program so that the single processing circuit executes the programs. Alternatively, the specific functions may be installed in dedicated independent program-executing circuits.

The term "processor" used in the explanation above denotes, for example, a Central Processing Unit (CPU), a Graphical Processing Unit (GPU), or a circuit such as an Application Specific Integrated Circuit (ASIC), a programmable logic device (e.g., a Simple Programmable Logic Device [SPLD], a Complex Programmable Logic Device [CPLD]), or a Field Programmable Gate Array (FPGA). Each of the processors realizes the function thereof by reading and executing a corresponding one of the programs stored in the storage circuit 37A. Alternatively, it is also acceptable to directly incorporate the program into the circuit of each of the processors, instead of having the programs stored in the storage circuit 37A. In that situation, each of the processors realizes the function thereof by reading and executing the program incorporated in the circuit thereof. The first setting function 42, the selecting function 39A, and the controlling function 36A serve as examples of the first setting unit, the selecting unit, and the controlling unit, respectively.

The input equipment 31A includes a mouse, a keyboard, a button, a pedal (a foot switch), and/or the like used by an operator of the X-ray CT apparatus to input various types of instructions and various types of settings. The input equipment 31A is configured to transfer information about the instructions and the settings received from the operator to the processing circuit 40A so that the information is used for processes performed by the controlling function 36A.

The display 32A is a monitor referred to by the operator and is configured to display X-ray CT image data and the like for the operator and to display a Graphical User Interface (GUI) used for receiving the various types of instructions, the various types of settings, and the like from the operator via the input equipment 31A, under control of the controlling function 36A included in the processing circuit 40A. For example, to a GUI used for registering medical examination information, the operator inputs medical examination information such as the body posture during an image taking process performed on the patient P who is placed on a couchtop 22 illustrated in FIG. 5, by using the input equipment 31A.

By employing a scan controlling unit 33, the processing circuit 40A controls the projection data acquiring process performed by the gantry 10, by controlling operations of the X-ray radiation controlling circuit 11, the gantry driving circuit 16, the acquiring circuit 14, and couch driving equipment 21 (explained later), under the control of the controlling function 36A (explained later).

The storage circuit 37A has stored therein the programs for implementing the processing functions included in the processing circuit 40A. Further, the storage circuit 37A has stored therein data necessary for executing the program used for implementing the processing functions included in the processing circuit 40A. Further, the storage circuit 37A has stored therein an operation history of the X-ray CT apparatus performed by the operator, in the form of data.

The processing circuit 40A is configured to exercise overall control of the X-ray CT apparatus by controlling operations of the gantry 10, the couch 20, and the gantry-side interface 50, while employing the controlling function 36A. More specifically, the processing circuit 40A controls image taking processes performed by the gantry 10 by controlling the scan controlling function 33A while employing the controlling function 36A. Further, the processing circuit 40A is configured to exercise control so that the display 32A displays various types of image data stored in the storage circuit 37A by employing the controlling function 36A. Further, the processing circuit 40A is configured to communicate with the console equipment 30, to transmit data to the console equipment 30 and to obtain data from the console equipment 30, by employing the controlling function 36A.

The processing circuit 40A includes a selecting function 39A and the first setting function 42. Processes performed by these functions will be explained later.

Figure 4:
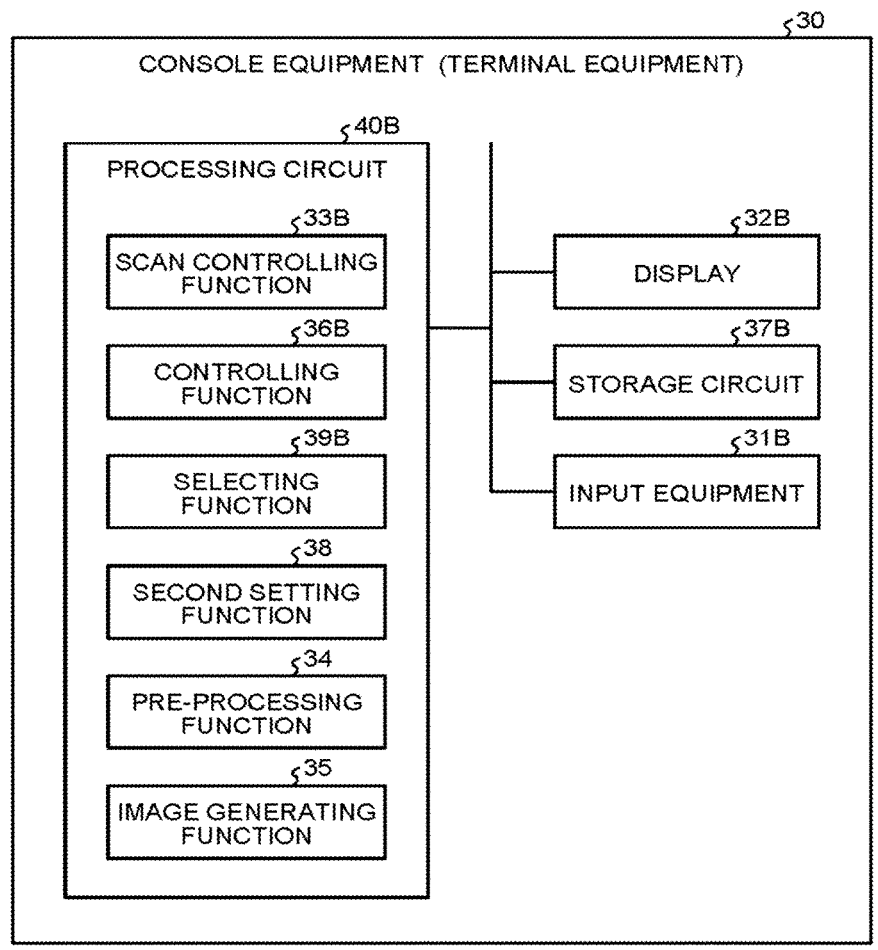

FIG. 4 illustrates a schematic configuration of the console equipment 30. The console equipment 30 is the same equipment as, or similar equipment to, the gantry-side interface 50, but is installed on the operation room side. In other words, the console equipment 30 is equipment configured to receive, in the operation room, operations performed by the operator on the X-ray CT apparatus. In addition, for example, the console equipment 30 is configured to reconstruct X-ray CT image data from the X-ray d detection data acquired by the gantry 10. The console equipment 30 includes a display 32B, a storage circuit 37B, input equipment 31B, and the processing circuit 40B. The processing circuit 40B includes, for example, a scan controlling function 33B, a controlling function 36B, a second setting function 38, the pre-processing function 34, and an image generating function 35. In certain embodiments, the processing circuit 40B may include a selecting function 39B.

Similarly to the description of the gantry-side interface 50, processing functions implemented by constituent elements such as the scan controlling function 33B, the controlling function 36B, the selecting function 39B, the second setting function 38, the pre-processing function 34, and the image generating function 35 are stored in the storage circuit 37B in the form of computer-executable programs. Similarly, the processing circuit 40B is a processor configured to realize the functions corresponding to the programs by reading and executing the programs from the storage circuit 37B. In other words, it means that the processing circuit 40B that has read the programs has the functions illustrated within the processing circuit 40B in FIG. 4. Similarly, another arrangement is acceptable in which the processing circuit 40B is structured by combining together a plurality of independent processors, so that the processors realize the functions by executing the programs.

The term "processor" used in the explanation above includes the same configuration as that explained in the description of the gantry-side interface 50. Each of the processors realizes the function thereof by reading and executing a corresponding one of the programs stored in the storage circuit 37B. Alternatively, it is also acceptable to directly incorporate the program into the circuit of each of the processors, instead of having the programs stored in the storage circuit 37B. In that situation, each of the processors realizes the function thereof by reading and executing the program incorporated in the circuit thereof. The second setting function 36, the selecting function 39B, and the controlling function 36B serve as examples of the second setting unit, the selecting unit, and the controlling unit, respectively.

The display 32B is a monitor referred to by the operator. The display 32B, for example, has the same configuration as that of the display 32A. Under control of the controlling function 36B included in the processing circuit 40B, the display 32B is configured to display the X-ray CT image data and the like for the operator and to display a GUI used for receiving the various types of instructions and the various types of settings from the operator via the input equipment 31B.

The storage circuit 37B has stored therein pieces reconstructing-purpose projection data generated by the processing circuit 40B by employing the pre-processing function 34. Further, the storage circuit 37B has also stored therein the pieces of projection data themselves acquired by the acquiring circuit 14. In this situation, the storage circuit 37B has stored therein X-ray tube positions in correspondence with the pieces of projection data generated by the processing circuit 40B while employing the pre-processing function 34 and the pieces of projection data generated by the acquiring circuit 14.

The input equipment 31B, for example, has the same configuration as that of the input equipment 31A and is configured to transfer information about the instructions and the settings received from the operator to the processing circuit 40B so that the information is used for processes performed by the controlling function 36B.

The processing circuit 40B is configured to control the projection data acquiring process performed by the gantry 10 by controlling operations of the X-ray radiation controlling circuit 11, the gantry driving circuit 16, the acquiring circuit 14, and the couch driving equipment 21, while employing the scan controlling function 33B under the control of the controlling function 36B (explained later).

The processing circuit 40B is configured to exercise overall control of the X-ray CT apparatus by controlling operations of the gantry 10, the couch 20, and the console equipment 30, while employing the controlling function 36B. More specifically, the processing circuit 40B controls image taking processes performed by the gantry 10 by controlling the scan controlling function 33B while employing the controlling function 36B. Further, the processing circuit 40B is configured to control image reconstructing processes and image generating processes performed by the console equipment 30, by controlling the pre-processing function 34 and the image generating function 35, while employing the controlling function 36B. Further, the processing circuit 40B is configured to exercise control so that the display 32B displays the various types of image data stored in the storage circuit 37B by employing the controlling function 36B. Further, the processing circuit 40B is configured to communicate with the gantry-side interface 50, to transmit data to the gantry-side interface 50 and to obtain data from the gantry-side interface 50, by employing the controlling function 36B.

In certain embodiments, the processing circuit 40B may include the selecting function 39B. Further, the processing circuit 40B includes the second setting function 38. Processes performed by these functions will be explained later.

By employing the pre-processing function 34, the processing circuit 40B is configured to generate corrected projection data by performing correcting processes such as a logarithmic converting process, an offset correcting process, a sensitivity correcting process, and a beam hardening correcting process, on the projection data generated by the acquiring circuit 14 during a main image taking process. In the following selections, the corrected projection data that is related to the main image taking process and is generated by the processing circuit 40B while employing the pre-processing function 34 will be referred to as reconstructing-purpose projection data.

The processing circuit 40B is a processing unit configured to generate various types of image data by using the projection data stored in the storage circuit 37B, by employing the image generating function 35. The processing circuit 40B has an image reconstructing function.

The processing circuit 40B is configured to reconstruct the X-ray CT image data by using the reconstructing-purpose projection data stored in the storage circuit 37B, while employing the image generating function 35. There are various reconstructing methods including a back projection process, for example. Further, examples of the back projection process include a back projection process realized by implementing a Filtered Pack Projection (FBP) method. Alternatively, the processing circuit 40B may reconstruct the X-ray CT image data by icing a successive approximation method, by employing the image generating function.

By employing the image generating function 35, the processing circuit 40B is able reconstruct three-dimensional X-ray CT image data by using projection data acquired by performing a helical scan, a conventional scan performed by using the X-ray detector 13 configured with the planar detector, or a step-and-shoot conventional scan. For example, by employing the image generating function 35, the processing circuit 40B reconstructs the three-dimensional X-ray CT image data as tomographic image data taken on a plurality of axial planes. The tomographic image data may be used as display-purpose two-dimensional X-ray CT image data. Further, by employing the image generating function 35, the processing circuit 40B generates display-purpose two-dimensional X-ray CT image data from the three-dimensional X-ray CT image data by performing various types of rendering processes thereon. Examples of the rendering processes include a process to reconstruct Multi Planar Reconstruction (MPR) image data taken on an arbitrary cross-sectional plane from the three-dimensional X-ray CT image data, by implementing a Multi Planar Reconstruction (MPR) method. Other examples of the rendering processes include a process to generate Volume Rendering (VR) image data or Maximum Intensity Projection (MIP) image data reflecting three-dimensional information from the three-dimensional X-ray CT image data, by performing a Volume Rendering (VR) process or implementing a Maximum Intensity Projection (MIP) method.

Figure 5:
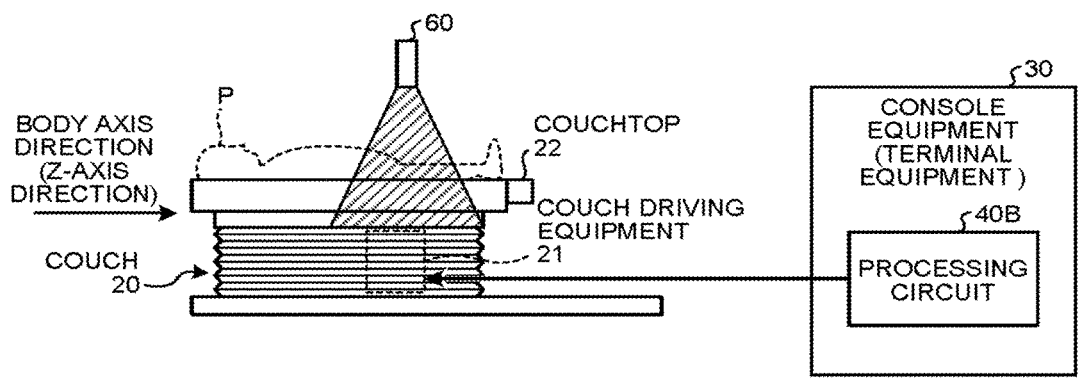

FIG. 5 illustrates a schematic configuration of the couch 20. The couch 20 is equipment on which the subject P is placed and includes the couchtop 22 and the couch driving equipment 21. The couchtop 22 is a board on which the subject P is dared. The couch driving equipment 21 is configured to move the subject P to the inside of the rotating frame 15 (into an image taking space) by moving the couchtop 22 in the Z-axis direction, either under the control of the processing circuit 40A implementing the controlling function 36A or under the control of the processing circuit 40B implementing the controlling function 36B.

During a main image taking process, for example, the gantry 10 performs a helical scan by which the subject P is helically scanned by causing the rotating frame 15 to rotate while the couchtop 22 is being moved. In another example, during a main image taking process, the gantry 10 performs a conventional scan by which the subject P is scanned on a circular orbit by causing the rotating frame 15 to rotate, while the position of the subject P is being fixed after the couchtop 22 is moved. In yet another example, during a main image taking process, the gantry 10 implements a step-and-shoot method by which a conventional scan is performed in multiple scan areas, by moving the position of the couchtop 22 at regular intervals.

An area display light projector 60 is equipment configured to enable the operator to check approximately how large an image taking area is, by emitting light onto the subject P. In an example, the area display light projector 60 emits the light within the range of a predetermined region, by adjusting an aperture attached to the area display light projector 60. By checking the light emitted so as to be superimposed on the body surface of the subject P, the operator is able to check whether the center position of the image taking area is not out of alignment and whether the image taking area is not too small or too large. In this situation, for example, the image taking area may denote an X-ray exposure area or may denote a reconstruction area. Examples of light sources that can be used as the area display light projector 60 include an LED light projector, a mercury lamp light projector, a halogen lamp, and other light projectors.

By employing the controlling function 36A (or the controlling function 36B), the processing circuit 40A (or the processing circuit 40B) is able to automatically arrange the illumination area of the light emitted from the area display light projector 60 to be in conjunction with an image taking condition setting. In that situation, by employing the controlling function 36A, the processing circuit 40A sets an illumination area corresponding to an X-ray exposure area (or a reconstruction area) under the current image taking condition setting as the light illumination area of the area display light projector 60. Conversely, when the operator has changed the light illumination area of the area display light projector 60, the processing circuit 40A changes the X-ray exposure area so as to match the light illumination area resulting from the operator's change, by employing the controlling function 36A. Details of these processes will be explained later.

Schematic configurations of some of the constituent elements of the X-ray CT apparatus according to the first embodiment have thus been explained; however, possible embodiments are not limited to this example.

For example, when the processing circuit 40B illustrated in FIG. 4 includes the pre-processing function 34 and the image generating function 35, i.e., when the image reconstructing process is performed by the console equipment 30, possible embodiments are not limited to the example above. For instance, the console equipment 30 may have only functions as a display terminal, so that a computer server that is connected to a network and receives data from the acquiring circuit 14 included in the gantry 10 performs the image reconstructing process and so that an output image resulting from the reconstructing process is transmitted to the console equipment 30 to be displayed thereby.

Further, the example is explained above in which the gantry-side interface 50 includes the display 32A and includes the keyboard and the like as the input equipment 31A; however, possible embodiments are not limited to this example. For instance, the gantry-side interface 50 may be a simple interface such as a switch and/or a button.

Next, a technical background of the X-ray CT apparatus according to the embodiment will briefly be explained.

Examples of methods used for performing image taking processes by using an X-ray CT apparatus include a method by which image taking conditions (e.g., an image taking area of the subject P) are set on the console equipment 30 side and another method by which the image taking conditions are set on the gantry 10 side. Usually, because the gantry-side interface 50 provided on the gantry 10 side is often a simpler interface than the console equipment 30, the image taking conditions are usually set on the console equipment 30 side that is more suitable for configuring complex settings. However, there are some situations where it desirable to set the image taking conditions on the gantry 10 side. For example, adjusting the image taking area of the subject P involves adjusting the position of the couch for the subject P, the operator (a radiologist) is often present on the gantry 10 (the scan room) side, rather than on the console equipment 30 (the operation room) side. When the X-ray CT apparatus was configured so that it is possible to set the image taking conditions only on the console equipment 30 side, it would unbearably be cumbersome for the operator to go back and forth between the operating room and the scan room to set the image taking condition, especially when, for example, the console equipment 30 and the gantry 10 are positioned physically distant from each other.

Accordingly, for image taking processes, it is desirable to be able to complete the image taking condition setting process only with operations performed on the gantry 10 side, as necessary. Needless to say, for image taking processes, it is also desirable to be able to complete the image taking condition setting process only with operations performed on the console equipment 30 side.

However, when it is possible to set the image taking conditions both on the gantry 10 side and on the console equipment 30 side, there is a possibility that an image taking process may be performed by using image taking conditions that are not intended by the operator, unless it is clearly defined which side (either the gantry 10 side or the console equipment 30 side) provides information used for setting the image taking conditions. For example, let us discuss a situation where there are two technicians in total, one on the gantry 10 side and the other on the console equipment 30 side, so that the technicians collaborate with each other to perform a medical examination. In that situation, when it is possible to set the image taking conditions both on the gantry 10 side and on the console equipment 30 side, an image taking process may be performed under image taking conditions that are not intended when the two technicians fail to communicate with each other very well, which may lead to a failure of the medical examination.

To cope with the circumstances described above, the X-ray CT apparatus according to the first embodiment is configured to receive, from the operator, an input of selection information that is information selecting from between an input of an image taking condition made on the gantry 10 side and an input of an image taking condition made on the console equipment 30 side as an input used for performing the image taking process on the subject P and to further perform the image taking process on the subject P on the basis of the received selection information. In other words, during an image taking planning process, by employing the selecting function 39A (or the selecting function 39B), the processing circuit 40A (or the processing circuit 40B) receives the input of the selection information indicating which setting function is able to confirm the image taking condition between the first setting function 42 and the second setting function 38 and to further cause the gantry 10 to perform the image taking process on the basis of the selection information received by selecting function. With this arrangement, it is possible set the image taking condition not only on the console equipment 30 side, but also on the gantry 10 side.

Figure 6:
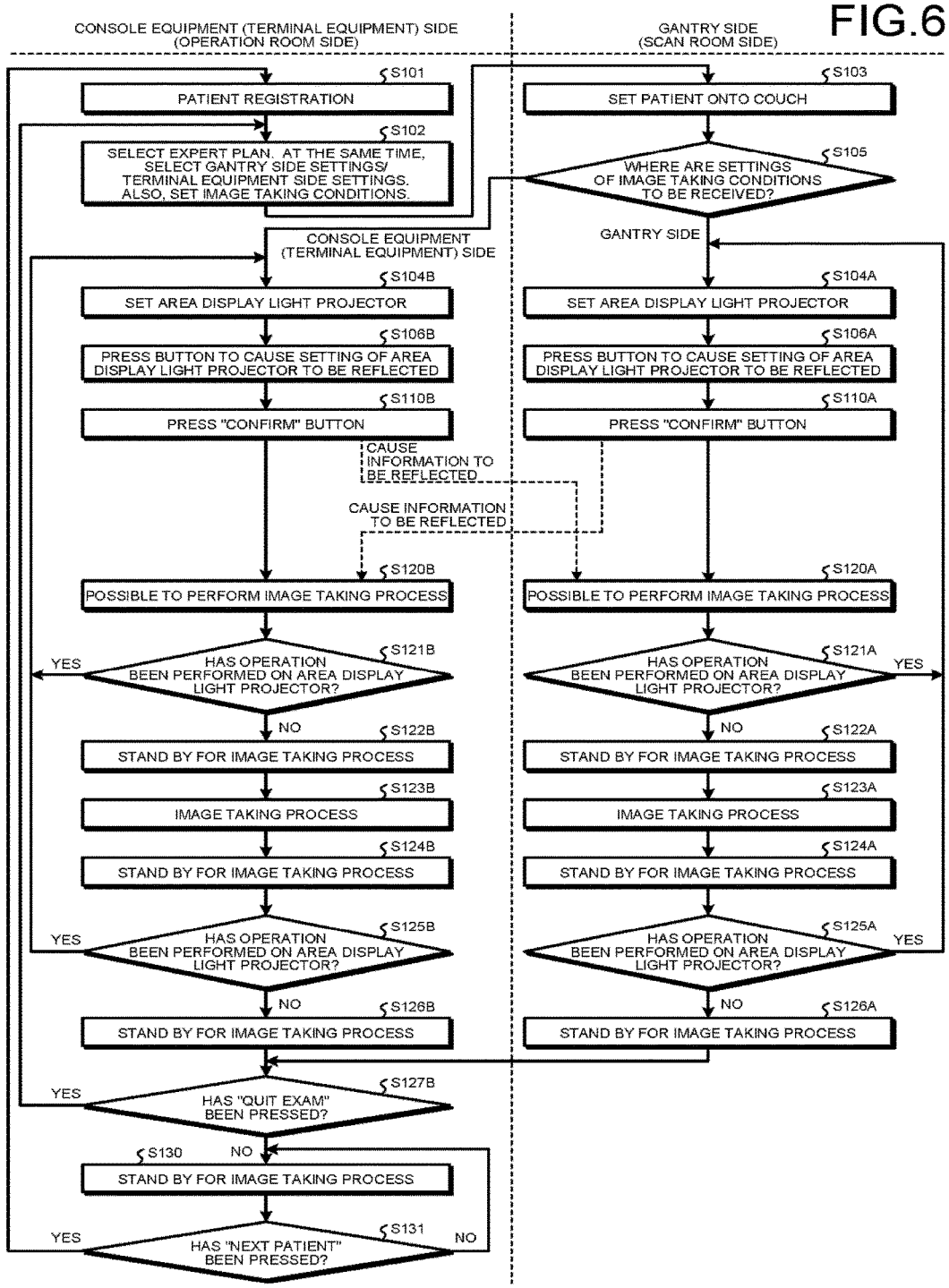
FIG. 6 is a flowchart for explaining a flow in a process performed by an X-ray CT apparatus according to a first embodiment.
Figure 7:
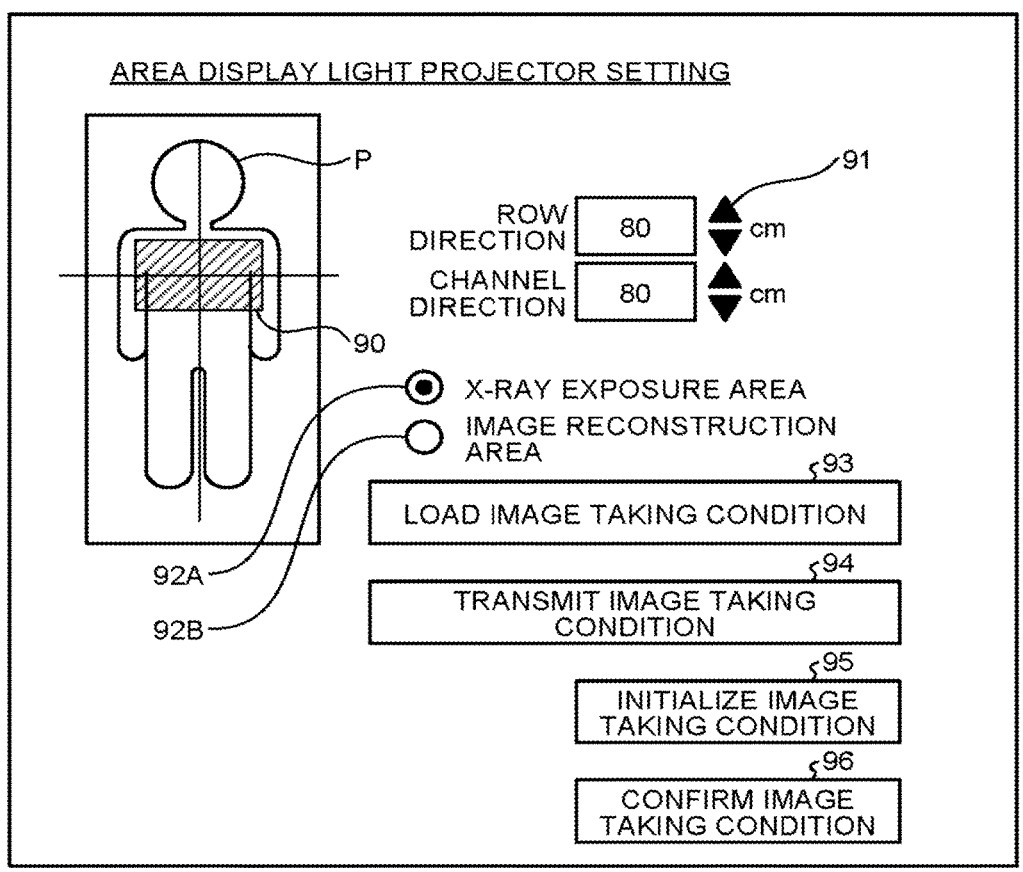
FIG. 7 is a drawing of an example of a screen design for an area display light projector setting process performed by the X-ray CT apparatus according to the first embodiment.

The technical feature described above will further be explained with reference to FIG. 6, together with FIG. 7 as necessary. FIG. 6 is a flowchart for explaining a flow in a process performed by the X-ray CT apparatus according to the first embodiment. Further, FIG. 7 is a drawing of an example of a screen design for an area display light projector setting process performed by the X-ray CT apparatus according to the first embodiment.

In the flowchart in FIG. 6, first of all, a patient registration process is performed on the console equipment 30 (the terminal equipment) side. In other words, the processing circuit 40B included in the console equipment 30 performs the patient registration process via the input equipment 31B (step S101). More specifically, the processing circuit 40B receives inputs of the patient's name, the patient's ID, and the like from the operator via the input equipment 31B.

Subsequently, by employing the controlling function 36B, the processing circuit 40B receives, from the operator, an input of a selection from expert plans related to the image taking processes to be performed on the subject P (step S102). In this situation, the expert plans denote various image taking conditions serving as preset conditions in an image taking plan. In this situation, the image taking conditions include both image taking conditions in a narrower sense that are the conditions used during the image taking processes and image generating conditions such as reconstructing conditions. Specific examples of the image taking conditions include an X-ray tube voltage, an X-ray tube current, a rotating speed of the rotating frame 15, a slice thickness, a value indicating the quantity of rows (hereinafter, "the number of rows"), and various reconstructing conditions. The processing circuit 40B presents the operator with a plurality of candidates for the preset conditions by causing the display 32B to display the plurality of candidates for the preset conditions, via the display 32B. When the operator has selected one of the plurality of preset conditions via the input equipment 31B, the processing circuit 40B sets the selected one of the preset conditions as an image taking condition for the subject P, by employing the controlling function 36B.

Further, via the display 32B, the processing circuit 40B presents the operator with the plurality of candidates for the preset conditions and further receives, by employing the selecting function 39B, an input of selection information (flag information) via the input equipment 31B provided on the console equipment 30 side. In this situation, the selection information is information selecting from between the gantry 10 aide and the console equipment 30 side (the terminal equipment side), as the side on which the image taking condition is to be set. In other words, the selection information is the information selecting from between first image taking conditions received as an input from the operator on the gantry 10 side and second image taking conditions received as an input from the operator on the console equipment 30 side, as the image taking conditions used by the gantry 10 for performing the image taking process on the subject P (e.g., selecting from between the gantry 10 side and the console equipment 30 side as the side on which a radiation exposure start button is to be validated). When the selection information (the flag information) is input by the operator, the processing circuit 40B brings the flag information related to either the first setting function 42 or the second setting function 38 into correspondence, as the selection information, with one or more preset conditions among the plurality of preset conditions that are selectable in the image taking plan. In this situation, the selection information (the flag information) does not necessarily have to be determined by an input from the operator. The selection information may be incorporated in advance in the candidates for the preset conditions described above so as to be set as one of the preset conditions.

For example, when the selection information is information indicating that the image taking processes are to be performed on the subject by using the first image taking conditions set on the gantry 10 side, the processing circuit 40A causes, at step S123A and so on described below, the gantry 10 to perform the image taking processes on the subject P by using the first image taking conditions set on the gantry 10 side, on the basis the selection information, by employing the controlling function 36A. Conversely, when the selection information is information indicating that the image taking processes are to be performed on the subject P by using the second image taking conditions set on the console equipment 30 side, the processing circuit 40B causes, at step S123B and so on described below, the gantry 10 to perform the image taking processes on the subject P by using the second image taking conditions set on the console equipment 30 side, on the basis of the selection information, by employing the controlling function 36B.

Further, the selection information also serves as information selecting from between the gantry 10 side and the console equipment 30 side as the side on which operations from the operator are to be received with regard to starting the image taking process, i.e., starting the radiation of the X-rays. For example, when the selection information is information indicating that the image taking processes are to be performed on the subject P by using the first image taking conditions set on the gantry 10 side, the gantry 10 receives an image taking process starting operation from the operator only on the gantry 10 side and does not receive (invalidates) any image taking process starting operation from the operator performed on the console equipment 30 side. Conversely, when the selection information is information indicating that the image taking processes are to be performed on the subject P by using the second image taking conditions set on the console equipment 30 side, the gantry 10 receives an image taking process starting operation from the operator only on the console equipment 30 side and does not receive (invalidates) any image taking process starting operation from the operator on the gantry 10 side.

By employing the selecting function 39B, when the processing circuit 40B has received an input of the selection information from the operator via the input equipment 31B, the processing circuit 40B further receives an input of more image taking conditions from the operator continuously via the input equipment 31B, by employing the controlling function 36B (step S102). In this situation, the "more image taking conditions" denote various image taking conditions other than the image taking area of the subject P such as, for example, the voltage applied to the X-ray tube 12a, the X-ray tube current of the X-ray tube 12a, the rotating speed of the rotating frame 15, the slice thickness, the number of rows, various reconstructing conditions, and the like.

In the first embodiment, of these various image taking conditions, the image taking condition called "image taking area of the subject P" is handled separately. More specifically, as for the "image taking area of the subject P", the condition is set on the side selected by the operator from between the gantry 10 side and the console equipment 30 side, on the basis of the selection information. In contrast, as for the image taking conditions other than the "image taking area of the subject P", the conditions are set on the console equipment 30 side, at step S102 by the controlling function 36B included in the processing circuit 40B.

By employing the controlling function 36B, when the processing circuit 40B has completed receiving the input from the operator about the image taking conditions other than the "image taking area of the subject P" at step S102, the gantry 10 subsequently receives an operation performed on the gantry 10 from the operator. The gantry 10 sets the subject P onto the couch 20 (step S103). More specifically, the operator who is operating the X-ray CT apparatus according to the embodiment places the subject P on the couchtop 22 of the couch 20. By employing the controlling function 36A, the processing circuit 40A receives an operation to move the position of the couchtop 22 of the couch 20 from the operator. By operating on the couchtop 22 of the couch 20, the operator moves the couchtop 22 in such a manner that the center of the image taking region for the subject P substantially coincides with the center of the X-ray exposure region.

When the process at step S103 is completed, by employing the selecting function 39A, the processing circuit 40A determines whether the processes thereafter are to be performed on the gantry 10 side or the console equipment 30 side, on the basis of the selection information received as an input by the processing circuit 40B at step S102 while employing the selecting function 39B (step 105). When the selection information is information indicating that the image taking processes are to be performed on the subject P by using the first image taking conditions set on the gantry 10 side, i.e., indicating that the processes are to be performed on the gantry 10 side, the processes thereafter at steps S104A through S126A will be performed on the gantry 10 side. In contrast, when the selection information is information indicating that the image taking processes are to be performed on the subject P by using the second image taking conditions set on the console equipment 30 side, i.e., indicating that the processes are to be performed on the console equipment 30 side, the processes thereafter at steps S104B through S126B will be performed on the console equipment 30 side.

First, an example in which the selection information is information indicating that the processes are to be performed on the gantry 10 side, i.e., the processes at steps S104A through S126A, will be explained.

The processing circuit 40A included in the gantry-side interface 50 provided on the gantry 10 side receives an operation performed on the area display light projector 60 provided on the gantry 10 side, by employing the first setting function 42 configured to receive the input of the first image taking conditions set for the subject P on the gantry 10 side.

For example, by employing the first setting function 42, the processing circuit 40A may receive the operation performed on the area display light projector 60 via a predetermined operation button. In another example, by employing the first setting function 42, the processing circuit 40A may receive the operation performed on the area display light projector 60 via a user interface including the input equipment 31A such as a keyboard and/or a mouse, the display 32A, and the like.

FIG. 7 illustrates an example of a screen design for the area display light projector 60 setting process performed by the X-ray CT apparatus according to the first embodiment. The screen illustrated in FIG. 7 is, for example, a screen displayed on the display 32A or the display 32B.

As illustrated in FIG. 7, for example, by employing the first setting function 42, the processing circuit 40A causes the display 32A to display data obtained by imaging the subject P in a real-time manner from the direction of the ceiling by using an optical camera (not illustrated). From the data obtained by the optical camera, the operator is able to recognize the area of the light emitted by the area display light projector 60 as, for example, a region 90 superimposed on the body surface of the subject P.

Via the user interface illustrated in FIG. 7, the processing circuit 40A receives, from the operator, a change to be made on the area of the light emitted by the area display light projector 60. For example, the current area of the light emitted by the area display light projector 60 has a size of "80 cm" in the row direction by "80 cm" in the channel direction. When the operator clicks on a button 91, for example, the area of the light emitted by the area display light projector 60 is changed to have a size of "90 cm" in the row direction by "80 cm" in the channel direction. Thus, the processing circuit 40A has received the change in this manner, for example.

Further, when the operator clicks on a button 93, the processing circuit 40A obtains, by employing the first setting function 42, the image taking condition under which the processing circuit 40A controls the X-ray radiation controlling circuit 11 by employing the controlling function 36A and further causes the obtained image taking condition to be reflected on the screen as a temporary value for the area of the light emitted by the area display light projector 60. For instance, let us discuss an example in which, by employing the controlling function 36A, the processing circuit 40A transmits a control signal to the X-ray radiation controlling circuit 11 so as to yield an X-ray radiation angle or the like that arranges the X-ray exposure area to have a size of "80 cm" in the row direction by "80 cm" in the channel direction. In that situation, the processing circuit 40A assesses that, under the current image taking condition, the X-ray exposure area will have a size of "80 cm" in the row direction by "80 cm" in the channel direction and further sets, by employing the first setting function 42, temporary values for the area of the light emitted by the area display light projector 60 to be "80 cm" in the row direction by "80 cm" in the channel direction.

Further, when the operator clicks on a button 95, the processing circuit 40A initializes the temporary values for the area of the light emitted by the area display light projector 60 to initial values that are preset in advance, by employing the first setting function 42.

Further, when the operator operates on radio buttons 92A and 92B, by employing the first setting function 42, the processing circuit 40A is able to switch between one mode in which temporary values for the area of the light emitted by the area display light projector 60 are determined on the basis of the X-ray exposure area under the X-ray tube current, the X-ray tube voltage, the radiation angle, and the like in the current settings and the other mode in which temporary values for the area of the light emitted by the area display light projector 60 are determined on the basis of the size of an image reconstruction possible area under X-ray tube current, the X-ray tube voltage, the radiation angle, and the like in the current settings.

Further, when the operator clicks on a button 94, the processing circuit 40A confirms the area of the light emitted by the area display light projector 60 to be the temporary values currently set on the user interface illustrated in FIG. 7, by employing the first setting function 42. At this me, by employing the first setting function 42, the processing circuit 40A transmits the confirmed values indicating the size of the area of the emitted light to the area display light projector 60. The area display light projector 60 emits light on the basis of the values obtained from the processing circuit 40A. The light emitted by the area display light projector 60 in this manner is captured by the optical camera described above, so that the operator is able to recognize the area of the light emitted by the area display light projector 60, as the area is being superimposed on the body surface of the subject P.

In this manner, by employing the first setting function 42, the processing circuit 40A adjusts the image taking area of the subject P, by receiving the operation performed on the area display light projector 60 (step S104A).

By employing the first setting function 42, the processing circuit 40A receives, from the operator, an input of a click on a button 96 (a button to cause the setting of the area display light, projector 60 to be reflected), which is a button indicating that the image taking area adjusting process has been finished and that the image taking condition (the size of the image taking area) confirmed. When the operator clicks on the button 96 which is the button to cause the setting of the area display light projector 60 to be reflected (step S106A), the processing circuit 40A sets, by employing the first setting function 42, the adjusted image taking area as an image taking condition included in the first image taking conditions and thus confirms the size of the "image taking area of the subject P".

Subsequently, by employing the first setting function 42, the processing circuit 40A receives, from the operator, an input of a click on a "CONFIRM" button (not illustrated), which is a button indicating that the process of setting the image taking conditions other than the image taking area has been finished and that all the image taking conditions are confirmed. When the operator clicks on the "CONFIRM" button (step S110A), the processing circuit. 40A confirms all the image taking conditions, by employing the first setting function 42.

In the first embodiment, the image taking conditions other than the "image taking area of the subject P" were already determined and confirmed at step S102.

When the operator presses the "CONFIRM" button, the processing circuit 40A determines that it is now possible to perform the image taking process on the gantry 10 side, by employing the scan controlling function 33A (step S120A). In parallel to these processes, when the operator presses the "CONFIRM" button so that the input of the first image taking conditions is received from the operator, the processing circuit 40A transmits, by employing the controlling function 36A, the image taking conditions received as the input to the console equipment 30, so that the information is reflected into the console equipment 30 (the dotted arrow extending from step S110A). The console equipment 30 causes the display 32B to display the received information. In this manner, because the processing circuit 40A promptly transmits the setting information obtained from the gantry-side interface 50 to the console equipment 30 so that the setting information is reflected into the console equipment 30, it is possible to smoothly share the information when two or more medical staff members perform the image taking process together, for example.

Returning to the description of the processes performed on the gantry 10 side, subsequent to step S120A, the processing circuit 40A judges, by employing the controlling function 36A, whether a user operation performed on the area display light projector 60 was detected since the button to cause the setting of the area display light projector 60 to be reflected had been pressed at step S106A (step S121A). When no user operation has been detected (step S121A: No), because no particular problem occurred, the process proceeds to the next step. When a user operation has been detected (step 121A: Yes), because there is a high possibility that the operator may be trying to change the image taking area, the processing circuit 40A resets the image taking condition for the subject P and re-configures the image taking condition for the subject P, by employing the selecting function 39A. In that situation, the process returns to step S104A where the processing circuit 40A re-configures the setting of the area display light projector 60. More specifically, by employing the first setting function 42, the processing circuit 40A sets the image taking area adjusted by the user operation performed on the gantry 10 side after the image taking area was adjusted, as an image taking condition included in the first image taking conditions.

Returning to the description of the situation where the judgment result at step S121A is in the negative (step S121A: No), the processing circuit 40A goes into an image taking process standby state because the preparation for the image taking process is completed (step S122A) and further receives an input of an image taking process starting instruction via the input equipment 31A. When having received, from the operator, the input indicating that the image taking process be started, the processing circuit 40A transmits a predetermined signal to the X-ray radiation controlling circuit 11 and causes the gantry 10 to perform the image taking process on the basis of the selection information, by employing the controlling function 36A. As a result, the image taking process is started (step S123A). When the one image taking process has been finished, the processing circuit 40A goes into the image taking process standby state again, and subsequently receives an input of an image taking process starting instruction via the input equipment 31A (step S124A). Further, by employing the controlling function 36A, the processing circuit 40A judges whether or not a user operation performed on the area display light projector 60 has been detected (step S125A). When no user operation has been detected (step S125A: No), because no particular problem occurred, the process proceeds to the next step, and the processing circuit 40A goes into the image taking process standby state (step S126A). When a user operation has been detected (step S125A: Yes), the process returns to step S104A. As explained above, ho performing steps S121A through S126A, the processing circuit 40A performs the plurality of image taking processes contained in the one image taking plan for the one subject P, until all of the image taking processes are finished.

Next, returning to the description of step S105, another example in which the selection information is information indicating that the processes are to be performed on the console equipment 30 side, i.e., the processes at steps S104B through S126B, will be explained. Detailed explanations of some of the processes that are the same as those at steps S104A through S126A will be omitted.

At step S104B, the same process as that at step S104A is performed. In other words, the processing circuit 40B provided in the console equipment 30 configured to communicate with the gantry 10 receives, from the operator, an operation via the console equipment 30, by employing the second setting function 38 configured to receive the input of the second image taking conditions for the subject P. Similarly to step S104A, by employing the second setting function 38, the processing circuit 40B adjusts the image taking area of the subject P by receiving an operation performed on the area display light projector 60 while using the same user interface as explained with reference to FIG. 7, for example. In this situation, the processing circuit 40B implementing the second setting function 38 may adjust the image taking area on the screen, without going through the operation performed on the area display light projector 60.

Similarly, when the operator clicks on the button to cause the setting of the area display light, projector 60 to be reflected (step S106B), the processing circuit 40B sets the adjusted image taking area as an image taking condition included in the second image taking conditions and confirms the size of the "image taking area of the subject P", by employing the second setting function 38.

When the operator clicks on the "CONFIRM" button (step S110B), the processing circuit 40B confirms all the image taking conditions, by employing the second setting function 38. When having received the input of the second image taking conditions from the operator in this manner, the processing circuit 40B transmits the second image taking conditions to the gantry 10 by employing the controlling function 36B, so that the information is reflected into the gantry-side interface 50 (the dotted arrow extending from step S110B). As a result, it is now possible to perform the image taking process on the gantry 10 side (step S120B). The gantry-side Interface 50 causes the display 32A to display the received information. In this manner, because the processing circuit 40B promptly transmits the setting information obtained from the console equipment 30 to the gantry-side interface 50 so that the setting information is reflected into the gantry-side interface 50, it is possible to smoothly share the information when two or more medical staff members perform the image taking process together, for example.

Returning to the description of the process performed on the console equipment 30 side, the processing circuit 40B subsequently judges, by employing the controlling function 36B, whether a user operation performed on the area display light projector 60 was detected since the button to cause the setting of the area display light projector 60 to be reflected had been pressed at step S106B (step S121B). When no user operation has been detected (step S121B: No), because no particular problem occurred, the process proceeds to the next step. When a user operation has been detected (step S121B: Yes), because there is a high possibility that the operator may be trying to change the image taking area, the processing circuit 40B resets the image taking condition for the subject P and re-configures the image taking condition for the subject P, by employing the selecting function 39B. In that situation, the process returns to step S104B where the processing circuit. 40B re-configures the setting of the area display light projector 60. In other words, the X-ray CT apparatus according to the embodiment includes a changing unit (not illustrated) configured to change the flag information (the selection information) that is related to either the first setting function 42 or the second setting function 38 and is kept in correspondence with the preset conditions.

Returning to the description of the situation where the judgment result at step S121B is in the negative (step S121B: No), the processing circuit 40B goes into an image taking process standby state because the preparation for the image taking process is completed (step S122B) and further receives an input of an image taking process starting instruction via the input equipment 31B. When having received, from the operator, the input indicating that the image taking process be started, the processing circuit 40B transmits a predetermined signal to the X-ray radiation controlling circuit 11 and causes the gantry 10 to perform the image taking process on the basis of the selection information, by employing the controlling function 36B. As a result, the image taking process is started (step S123B).

When the one image taking process has been finished, the processing circuit 40B goes into the image taking process standby state again, and subsequently receives an input of an image taking process starting instruction via the input equipment 31B (step S124B). Further, by employing the controlling function 36B, the processing circuit 40B judges whether or not a user operation performed on the area display light projector 60 has been detected (step S125B). When no user operation has been detected (step S125B: No), because no particular problem occurred, the process proceeds to the next step, and the processing circuit 40B goes into the image taking process standby state (step S126B). When a user operation has been detected (step S125B: Yes), the process returns to step S104B. As explained above, by performing steps S121B through S126B, the processing circuit 40B performs the plurality of image taking processes contained in the one image taking plan for the one subject P, until all of the image taking processes are finished.

Next, processes at and after step S127B will be explained. When the operator presses the "QUIT EXAM" button, i.e., when an input is received indicating that the process based on the current expert plan (the predetermined preset conditions) is ended for now and that a new expert plan (predetermined preset conditions) is to be selected (step S127B: Yes), the process returns to step S102 where the processing circuit 40B re-selects the predetermined preset conditions via the input equipment 31B. When the operator does not press the "QUIT EXAM" button (step S127B: No), the process proceeds to the next step where the processing circuit 40B goes into the image taking process standby state (step S130).

When the operator presses the "NEXT PATIENT" button, i.e., when an input is received from the operator indicating that the image taking processes for the currently-imaged patient have all been finished and that a medical examination for the next patient is to be started (step S131: Yes), the process returns to step S101 where the next patient is registered. When the judgment result at step S131 is in the negative (step S131: No), the process returns to step S130 where the processing circuit 40B goes into the image taking process standby state.

A flow in the process performed by the X-ray CT apparatus according to the first embodiment has thus been explained; however, possible embodiments are not limited to this example.

In the embodiment, a case has been explained in which each of the processing circuit 40A and the processing circuit 40B is provided on the gantry 10 side and on the condole equipment 30 side, respectively, as independent processing circuits. However, embodiments are not limited to this example. As an example, the processing circuit 40A and the processing circuit 40B as a whole may be constructed as one processing circuit. In that case, the one processing circuit includes the processing circuit 40A (a first processing circuit) configured to adjust an image taking area of a subject by receiving an operation performed on the light projector and configured to set the adjusted image taking area as an image taking condition included in first, image taking conditions and the processing circuit 40B (a second processing circuit) configured to adjust an image taking area of the subject by receiving an operation from an operator via the terminal equipment and configured to set the adjusted image taking area as an image taking condition included in second image taking conditions.

The example is explained above in which the operations at steps S101 and S102 are performed on the console equipment 30 side (the terminal equipment side); however, possible embodiments are not limited to this example. For instance, the operations at steps S101 and S102 may be performed on the gantry 10 side. Further, the example is explained above in which the operation at step S105 is performed on the gantry 10 side; however, possible embodiments are not limited to this example. For instance, the operation at step S105 may be performed on the console equipment 30 side.

The example is explained above in which, to configure the setting of the area display light projector 60 (step S104A), the processing circuit 40A includes the interface as illustrated in FIG. 7; however, possible embodiments are not limited to this example. For instance, being able to input information from a keyboard or a mouse is not a requisite constituent element. It is acceptable to use a button and/or a switch as the input equipment 31A, for example. Further, the display 32A is not a requisite constituent element. For example, it is acceptable to configure output equipment with an LED lamp being in an ON state.

In the embodiment above, the example is explained in which, with regard to the image taking process starting instructions, the processing circuit 40A and the processing circuit 40B each receives the instructions only from the side selected by the selection information; however, possible embodiments are not limited to this example. For instance, another arrangement is possible in which the processing circuit 40A and the processing circuit 40B each receive instructions only from the side selected by the selection information with regard to changing the image taking area of the patient P, but each receives instructions from both the console equipment 30 side and the gantry 10 side with regard to the image taking process starting instructions.

Further, in the embodiment described above, the example is explained in which, for instance, to judge at steps S121B and S125B whether or not an operation has been performed on the area display light projector 60, only the operation performed on the side where the processes are taking place are subject to the judgment regarding the operation performed on the area display light projector 60; however possible embodiments are not limited to this example. For instance, at step S121B, when the operator performs an operation on the area display light projector 60 on the gantry 10 side, the processing circuit 40B may also determine that the judgment result at step S121B is in the positive (step S121B: Yes). Further, the timing with which the flag information that is related to either the first setting function 42 or the second setting function 38 and is kept in correspondence with the preset conditions is changed does not necessarily have to be at step S121B, step S125B, and so on. It is acceptable to change the flag information with any arbitrary timing.

Further, in that situation, the example is explained above in which the process returns to step S104A when the judgment result at step S121A is in the positive (step S121A: Yes) or when the judgment result at step S125A is in the positive (step S125A: Yes), and the process returns to step S104B when the judgment result at step S121B is in the positive (step S121B: Yes) or the judgment result at step 31258 is in the positive (step S125B: Yes), (i.e., when the processing circuit 40A or 40B has detected a user operation performed on the area display light projector 60, the image taking area is re-configured while selection information is fixed); however, possible embodiments are not limited to this example. For instance, the following arrangement is also possible: The processing circuit 40A judges whether or not a user operation performed on the area display light projector 60 has been detected, by employing the controlling function 36A. When a user operation has been detected, the processing circuit 40A receives an input of selection information again, by employing the selecting function 39A. On the basis of the newly-received selection information, the processing circuit 40A (or the processing circuit 40B) causes the gantry 10 to perform an image taking process by employing the controlling function 36A (or by employing the controlling function 36B). In other words, in the flowchart illustrated in FIG. 6, when the judgment result at step S121A is in the positive (step S121A: Yes) or when the judgment result at step S125A is in the positive (step S125A: Yes), the process may return to step S102 where the processing circuit 40B receives an input of selection information from the operator. In that situation, the process at step S103 may be omitted for the second time and thereafter. Further, although the processing circuit 40A is explained here, the same applies to the processing circuit 40B.

As explained above, the X-ray CT apparatus according to the first embodiment is configured to receive, from the operator, the input of the selection information that is the information selecting from between the gantry 10 side and the console equipment 30 side as the side on which the settings are to be configured. The X-ray CT apparatus is configured to further perform the image taking processes on the patient P on the basis of the received selection information. With this arrangement, it is possible to provide the X-ray CT apparatus that makes it possible to set the image taking conditions either on the gantry 10 side or on the console equipment 30 side.

Second Embodiment

The X-ray CT apparatus according to the first embodiment is configured to receive, from the operator, the input of the selection information selecting from between the gantry 10 side and the console equipment 30 as the side on which the image taking conditions are to be set and to further perform the image taking processes on the patient P on the basis of the received selection information. In the first embodiment, the selection information is related to the image taking area of the patient P. In contrast, in a second embodiment, also for the image taking conditions other than the image taking area of the patient P, settings are configured by using the selection information.

In the second embodiment, by employing the first setting function 42, the processing circuit 40A included in the gantry-side interface 50 is configured to further set at least one selected from an X-ray tube current, an X-ray tube voltage, a rotating speed of the rotating frame 15, a slice thickness, and the number of rows, as an image taking condition included in the first image taking conditions that are the image taking conditions set on the gantry 10 side. Further, by employing the second setting function 38, the console equipment 30 is configured to further set at least one selected from an X-ray tube current, an X-ray tube voltage, a rotating speed of the rotating frame 15, a slice thickness, and the number of rows, as an image taking condition included in the second image taking conditions that are the image taking conditions set on the console equipment 30 side. With these arrangements, it is possible to further improve the level of convenience for the operator.

The technical feature described above will further be explained with reference to FIG. 8. FIG. 8 is a flowchart for explaining a flow in a process performed by an X-ray CT apparatus according to the second embodiment. In FIG. 8, because the processes other than those at steps S102X, S107A, and S107B are the same as the processes illustrated in FIG. 6, detailed explanations thereof will be omitted.

In the flowchart in FIG. 8, first of all, the processing circuit 40B performs a patient registration process via the input equipment 31B, similarly to the first embodiment (step S101). Subsequently, by employing the controlling function 36B, the processing circuit 40B receives, from the operator, an input of a selection from the expert plans related to the image taking processes performed on the patient P. Further, the processing circuit 40B presents the operator with a plurality of candidates for the preset conditions via the display 32B and also receives, by employing the selecting function 39B, an input of selection information (flag information) via the input equipment 31B provided on the console equipment 30 side (step S102X).

Unlike in the first embodiment, in the second embodiment, after the processing circuit 40B receives, at step S102X, the input of the selection information from the operator via the input equipment 31B by employing the selecting function 39B, the processing circuit 40B does not receive any more inputs of image taking condition. Instead, when it is determined at steps S107A and S107B (explained later) where the settings of the image taking conditions are to be received (i.e., either on the console equipment 30 side or on the gantry 10 side) on the basis of the selection information, an input of the image taking conditions is further received in the selected location.

The gantry 10 sets the patient P onto the couch 20 (step S103). Similarly to the first embodiment, when the process at step S103 is completed, the processing circuit 40A including the selecting function 39A determines whether the processes thereafter are to be performed on the gantry 10 side or on the console equipment 30 side, on the basis of the selection information received as the input at step S102X by the processing circuit 40B including the selecting function 39B. In other words, the processing circuit 40A determines the location in which the settings of the image taking conditions are to be received (i.e., either on the gantry 10 side or on the console equipment 30 side) (step S105).

In the following sections, first, an example in which the selection information is information indicating that the processes are to be performed on the gantry 10 side, i.e., the processes at steps S104A through S126A, will be explained.

Similarly to the first embodiment, the setting of the area display light projector 60 is configured step S104A). In other words, by employing the first setting function 42, the processing circuit 40A adjusts the image taking area of the patient P by receiving an operation performed on the area display light projector 60. By employing the first setting function 42, the processing circuit 40A receives, from the operator, an input made on the button to cause the setting of the area display light projector 60 to be reflected. When the operator presses the button to cause the setting of the area display light projector 60 to be reflected (step S106A), by employing the first setting function 42, the processing circuit 40A sets the adjusted image taking area as an image taking condition included in the first image taking conditions and confirms the size of the "image taking area of the patient P".

Subsequently, by employing the first setting function 42, the processing circuit 40A sets the image taking conditions other than the "image taking area of the patient P" as image taking conditions included in the first image taking conditions that are the image taking conditions set on the gantry 10 side (step S107A). More specifically, by employing the first setting function 42, the processing circuit 40A further sets at least one selected from among the X-ray tube current, the X-ray tube voltage, the rotating speed of the rotating frame 15, the slice thickness, and the number of rows, as an image taking condition included in the first image taking conditions that are the image taking conditions set on the gantry 10 side.

Subsequently, by employing the first setting function 42, the processing circuit 40A receives, from the operator, an input of a click on the "CONFIRM" button (not illustrated) that is a button indicating that the process of setting the image taking conditions other than the image taking area has been finished and that all the image taking conditions are confirmed. When the operator clicks on the "CONFIRM" button (step S110A), the processing circuit 40A confirms both of the image taking conditions, namely, the "image taking area of the patient P" that is the image taking condition set at step S106A and the other image taking conditions set at step S107A, by employing the first setting function 42.

After that, at steps S110A through S126A, the X-ray CT apparatus according to the second embodiment performs the same processes as those performed by the X-ray CT apparatus according to the first embodiment.

Next, returning to the description of step S105, another example in which the selection information is information indicating that the processes are to be performed on the console equipment 30 side, i.e., the processes at steps S104B through S126B, will be explained.

Similarly to the first embodiment, the processing circuit 40B provided in the console equipment 30 configured to communicate with the gantry 10 receives an operation from the operator via the console equipment 30, by employing the second setting function 38 configured to receive an input of the second image taking conditions for the patient P (step S104B).

Subsequently, by employing the second setting function 38, the processing circuit 40B sets image taking conditions other than the "image taking area of the patient P" as image taking conditions included in the second image taking conditions that are the image taking conditions set on the console equipment 30 side (step S107B). More specifically, by employing the second setting function 38, the processing circuit 40B further sets at least one selected from among the X-ray tube current, the X-ray tube voltage, the rotating speed of the rotating frame 15, the slice thickness, and the number of rows, as image taking conditions included in the second image taking conditions that are the image taking conditions set on the console equipment 30 side.

After that, at steps S110B through S131, the X-ray CT apparatus according to the second embodiment performs the same processes as those performed by the X-ray CT apparatus according to the first embodiment.

A flow in the process performed by the X-ray CT apparatus according to the second embodiment, has thus been explained; however, possible embodiments are not limited to this example. For instance, the various modification examples explained in the first embodiment are also applicable to the second embodiment.

Further, the example is explained above in which, at step S102X, the processing circuit 40B including the controlling function 36B receives, from the operator, the input of the selection from the expert plans related to the image taking processes performed on the patient P; however, possible embodiments are not limited to this example. For instance, instead of at step S102X, the processing circuit 40B may receive, from the operator, the input of a selection from the expert plans at step S107B, by employing the controlling function 36B. Further, instead of the processing circuit 40B receiving, from the operator, the input of a selection from the expert plans at step S102X by employing the controlling function 36B, the processing circuit 40A may receive, from the operator, an input of a selection from the expert plans at step S107A by employing the controlling function 36A.

As explained above, the X-ray CT apparatus according to the second embodiment is configured to also set the various image taking conditions other than the image taking area of the patient P, on the side selected by the selection information from between the gantry 10 side and the console equipment 30 side. With this arrangement, there is a wider variety of image taking conditions that can be set on the gantry 10, and it is therefore possible to improve the level of convenience for the operator.

Third Embodiment

In the first embodiment, the example is explained in which, at step 3102 in FIG. 6, the processing circuit 40B including the controlling function 36B receives the input of a selection from the expert plans (the preset conditions in the image taking plan) related to the image taking process performed on the patient P. In other words, the expert plans presented to the operator are the conditions that are preset in advance, regardless of the target of the image taking processes.

In contrast, in a third embodiment, instead of the operator setting the image taking conditions when being presented with the conditions preset in advance, the operator is able to be presented with, after adjusting the image taking area by using the area display light projector 60, image taking conditions that are preset on the basis of a result of the image taking area adjustment. With this arrangement, the X-ray CT apparatus is able to present the operator with the conditions that are more appropriate for the target of the image taking processes.

More specifically, in the third embodiment, after adjusting the image taking area by receiving an operation performed on the area display light projector 60, the processing circuit 40A including the first setting function 42 sets first image taking conditions that are the image taking conditions set on the gantry 10 side, by selecting one or more preset conditions in the image taking plan from among a plurality of candidates. Also, after adjusting the image taking area by receiving a user operation via the console equipment 30 (the terminal equipment), the processing circuit 40B including the second setting function 38 sets second image taking conditions that are the image taking conditions set on the console equipment 30 side, by selecting one or more preset conditions in the image taking plan from among a plurality of candidates. In other words, after adjusting the image taking area by receiving the operation performed on the area display light projector 60 while employing the first setting function 42, the processing circuit 40A selects the one or more preset conditions from among the plurality of preset conditions related to the image taking area, on the basis of the adjusted image taking area and further presents the operator with the one or more selected preset conditions. Alternatively, after adjusting the image taking area by receiving the user operation via the console equipment 30 (the terminal equipment) while employing the second setting function 38, the processing circuit 40B selects the one or more preset conditions from among the plurality of preset conditions in the image taking plan, on the basis of the image taking area and further presents the operator with the one or more selected preset conditions. The operator then sets the image taking conditions on the basis of the presented information.

The technical feature described above will further be explained with reference to FIG. 9. FIG. 9 is a flowchart for explaining a flow in a process performed by the X-ray CT apparatus according to the third embodiment. In FIG. 9, because the processes other than those at steps S102Y, S150, S151A, and S151B are the same as the processes illustrated in FIG. 8, detailed explanations thereof will be omitted.

In the flowchart in FIG. 9, first of all, the processing circuit 40B performs a patient registration process via the input equipment 31B, similarly to the embodiments described above (step S101). Further, the processing circuit 40B presents the operator with a plurality of candidates for the preset conditions via the display 32B and also receives an input of selection information via the input equipment 31B provided on the terminal equipment side by employing the selecting function 39B (step S102Y).

Unlike in the first and the second embodiments, in the third embodiment, the processing circuit 40B, at step S102Y, does not receive an input of a selection from the expert plans related to the image taking processes performed on the patient P by employing the controlling function 36B. Instead, after it is determined at steps S151A and S151B (described later) where the settings of the image taking conditions are to be received (i.e., either on the console equipment 30 side or on the gantry 10 side) on the basis of the selection information (the flag information), an input of a selection from the expert plans is received in the determined location.

The gantry 10 sets the patient P onto the couch 20 (step S103). Subsequently, by using the area display light projector 60, an image taking area is set (step S150). In other words, the processing circuit 40A adjusts the image taking area by receiving an operation performed on the area display light projector 60 while employing the first setting function 42. Further, although not illustrated, by employing the second setting function 38, the processing circuit 40B may adjust the image taking area by receiving a user operation via the console equipment 30 side (the terminal equipment).

In other words, the process at step S150 is the same as the processes at steps S104A and S104B in the first and the second embodiments.

After that, when the process at step S150 is completed, similarly to the first and the second embodiments, the processing circuit 40A (or the processing circuit 40B) including the selecting function 39A (or the selecting function 39B) determines whether the processes thereafter are to be performed on the gantry 10 side or on the console equipment 30 side, on the basis of the selection information received as an input at step S102Y (step S105).

In the following sections, first, an example in which the selection information is information indicating that the processes are to be performed on the gantry 10 side, i.e., the processes at steps S151A through S126A, will be explained.

By employing the controlling function 36A, the processing circuit 40A receives, from the operator, an input of a selection from the expert plans related to the image taking processes performed on the patient P (step S151A). More specifically, by employing the first setting function 42, the processing circuit 40A selects one or more preset conditions in the image taking plan from among a plurality of candidates. Subsequently, by employing the first setting function 42, the processing circuit 40A receives, from the operator, an input made on the button to cause the setting of the area display light projector 60 to be reflected. When the operator presses the button to cause the setting of the area display light projector 60 to be reflected (step S106A), the processing circuit 40A sets, by employing the first setting function 42, the adjusted image taking area as an image taking condition included in the first image taking conditions and further confirms the size of the "image taking area of the patient P". As a result, by employing the first setting function 42, the processing circuit 40A sets the first image taking conditions that are the image taking conditions set on the gantry 10 side (step S107A).

The processes at steps S110A through S126A are the same as those explained in the second embodiment. Thus, the explanations thereof will be omitted.

Next, returning to the description of step S105, another example in which the selection information is information indicating that the processes are to be performed on the console equipment 30 side, i.e., the processes at steps S151B through S126B, will be explained.

By employing the controlling function 36B, the processing circuit 40B receives, from the operator, a selection from the expert plans related to the image taking processes performed on the patient P (step S131B). More specifically, by employing the second setting function 38, the processing circuit 40B selects one or more preset conditions in the image taking plan from among a plurality of candidates. By employing the second setting function 38, the processing circuit 40B receives, from the operator, an input made on the button to cause the setting of the area display light projector 60 to be reflected. When the operator presses the button to cause the setting of the area display light projector 60 to be reflected step S106B), by employing the second setting function 38, the processing circuit 40B sets the adjusted image taking area as an image taking condition included in the second image taking area and confirms the size of the "image taking area of the patient P". As a result, by employing the second setting function 38, the processing circuit 40B sets the second image taking conditions that are the image taking conditions set on the console equipment 30 side (step S107B).

The processes at steps S121B through S131 are the same as Those explained in the second embodiment. Thus, the explanations thereof will be omitted.

A flow in the process performed by the X-ray CT apparatus according to the third embodiment has thus been explained; however, possible embodiments are not limited to this example. For instance, the various modification examples explained in the first embodiment are also applicable to the third embodiment.

As explained above, the X-ray CT apparatus according to the third embodiment is configured to prompt the operator to select the one or more preset condition on the basis of the adjustment made by the operator on the image taking area while sing the area display light projector 60. With this arrangement, it is possible to present the operator with more appropriate preset conditions as the image taking conditions. It is therefore possible to improve the level of convenience for the operator.

Programs

The instructions indicated in the processing procedures described in the embodiments described above may be executed on the basis of a computer program (hereinafter, "program") realized with software. It is also possible to achieve the same advantageous effects as those achieved by the X-ray CT apparatuses described in the embodiments above, by configuring a generally-used computer system to store therein the program in advance and to read the program. The instructions described in the embodiments above are recorded as a computer-executable program on a recording medium such as a magnetic disk (a flexible disk, a hard disk, etc.), an optical disk (a Compact Disk Read-Only Memory [CD-ROM], a Compact Disk Recordable [CD-R], a Compact Disk Rewritable [CD-RW], a Digital Versatile Disk Read-Only Memory [DVD-ROM], a DVD±R, a DVD±RW, etc.), a semiconductor memory, or the like. As long as a computer or an incorporated system is able to read data from the storage medium, any storage format may be used. The computer is able to realize the same operations as those realized by the X-ray CT apparatuses in the embodiments described above, by reading the program from the recoding medium and causing a CPU to execute the instructions written in the program on the basis of the program. Needless to say, when obtaining or reading the program, the computer may obtain or read the program via a network.

Further, on the basis of the instructions in the program installed from the storage medium onto the computer or the incorporated system, an Operating System (OS) working in the computer or middleware (MW) such as database management software or a network may execute a part of the processes that realize any of the embodiments described above.

Further, the storage medium does not necessarily have to be a medium independent from the computer or the incorporated system. The storage medium may be a medium that stores therein or temporarily stores therein the program transferred and downloaded via a Local Area Network (LAN) or the Internet.

Further, the storage medium does not necessarily have to be a single storage medium. The storage medium according to any of the embodiments described above includes the situation where the processes in the embodiment are executed from two or more media. The medium or media may have any configuration.

Further, the computer or the incorporated system according to any the embodiments described above is configured to execute the processes described in the embodiment on the basis of the program stored in the storage medium or media.

Accordingly, the computer or the incorporated system may have any configuration and may be configured with a single apparatus such as a personal computer, a microcomputer, or the like, or may be configured with a system or the like in which a plurality of apparatuses are connected to one another via a network.

Further, the computer according to any of the embodiments does not necessarily have to be a personal computer. The computer may be an arithmetic processing unit included in an information processing device, a microcomputer, or the like. The term "computer" generally refers to any device or apparatus capable of realizing the functions described in the embodiments above by using a program.

According to at least one aspect of the embodiments described above, it is possible to provide the X-ray CT apparatus that makes it possible to set the image taking conditions intended by the operator, either on the gantry 10 side or on the console equipment 30 (terminal equipment) side.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray Computed Tomography (CT) apparatus, comprising:
   processing circuitry configured to
      adjust an image taking area of a subject by receiving an operation performed on a light projector provided on a gantry and set the adjusted image taking area as an image taking condition included in first image taking conditions, the gantry being configured to perform a CT image taking process on the subject with X-rays;
      adjust the image taking area of the subject by receiving an operation from an operator via terminal equipment and set the adjusted image taking area as an image taking condition included in second image taking conditions; and
      cause the gantry to perform an image taking process based on selection information selecting from between the first image taking conditions and the second image taking conditions as image taking conditions used for performing the image taking process on the subject.

2. The X-ray CT apparatus according to claim 1, wherein the processing circuitry is further configured to receive an input of the selection information during an image taking planning process and cause the gantry to perform the image taking process based on the received selection information.

3. The X-ray CT apparatus according to claim 1, wherein the processing circuitry includes a first processing circuit configured to adjust the image taking area of the subject by receiving the operation performed on the light projector and set the adjusted image taking area as the image taking condition included in the first image taking conditions, and a second processing circuit configured to adjust the image taking area of the subject by receiving the operation from the operator via the terminal equipment and set the adjusted image taking area as the image taking condition included in the second image taking conditions; and flag information related to the first processing circuit or the second processing circuit is kept in correspondence with, as the selection information, one or more preset conditions selected from among a plurality of preset conditions that are selectable during an image taking planning process.

4. The X-ray CT apparatus according to claim 3, wherein the processing circuitry is further configured to change the flag information that is related to the first processing circuit or the second processing circuit, the flag information being kept in correspondence with the one or more preset conditions.

5. The X-ray CT apparatus according to claim 1, wherein the processing circuitry includes a first processing circuit configured to adjust the image taking area of the subject by receiving the operation performed on the light projector and set the adjusted image taking area as the image taking condition included in the first image taking conditions, and a second processing circuit configured to adjust the image taking area of the subject by receiving the operation from the operator via the terminal equipment and set the adjusted image taking area as the image taking condition included in the second image taking conditions; and the processing circuitry is further configured to receive an input of the selection information selecting one from between the first processing circuit and the second processing circuit as a processing circuit to confirm the image taking condition.

6. The X-ray CT apparatus according to claim 1, wherein the processing circuitry includes a first processing circuit configured to adjust the image taking area of the subject by receiving the operation performed on the light projector and set the adjusted image taking area as the image taking condition included in the first image taking conditions, and a second processing circuit configured to adjust the image taking area of the subject by receiving the operation from the operator via the terminal equipment and configured to set the adjusted image taking area as the image taking condition included in the second image taking conditions; and at least one of the following is true:

after the first processing circuit adjusts the image taking area by receiving the operation performed on the light projector, the first processing circuit selects one or more preset conditions from among a plurality of preset conditions in an image taking plan based on the adjusted image taking area and further presents the operator with the one or more selected preset conditions; and after the second processing circuit adjusts the image taking area by receiving the operation from the operator via the terminal equipment, the second processing circuit selects one or more preset conditions from among a plurality of preset conditions in an image taking plan based on the adjusted image taking area and further presents the operator with the one or more selected preset conditions.

7. The X-ray CT apparatus according to claim 1, wherein the processing circuitry is further configured to set at least one of an X-ray tube current, an X-ray tube voltage, a rotating speed of a rotating frame, a slice thickness, and a value indicating a quantity of rows, as an image taking condition included in at least one of the first image taking conditions and the second image conditions.

8. The X-ray CT apparatus according to claim 1, wherein the processing circuitry is further configured to judge whether or not an operation performed by an operator on the light projector has been detected and, when the operation has been detected, reset the image taking condition for the subject and re-configure an image taking condition for the subject.

9. The X-ray CT apparatus according to claim 1, wherein the processing circuitry is further configured to receive an input of the selection information by using input equipment provided on the gantry side.

10. The X-ray CT apparatus according to claim 1, wherein the processing circuitry is further configured to judge whether or not an operation performed by an operator on the light projector has been detected and, when the operation has been detected, the processing circuitry newly receives an input of the selection information and further causes the gantry to perform the image taking process based on the newly received selection information.

11. The X-ray CT apparatus according to claim 1, wherein the processing circuitry is further configured to set an image taking area adjusted by a user operation performed on the gantry side after the image taking area was adjusted, as an image taking condition included in the first image taking conditions.

12. The X-ray CT apparatus according to claim 1, wherein when the processing circuitry has received an input of the first image taking conditions from an operator, the processing circuitry is configured to transmit the first image taking conditions to the terminal equipment.

* * * * *